US012801944B2

(12) United States Patent
Balaji et al.

(10) Patent No.: US 12,801,944 B2
(45) Date of Patent: Nov. 17, 2026

(54) METHODS AND SYSTEMS FOR DERIVING A BEHAVIOR KNOWLEDGE MODEL FOR DATA ANALYTICS

(71) Applicant: Tata Consultancy Services Limited, Mumbai (IN)

(72) Inventors: Ramesh Balaji, Chennai (IN); Swaminathan Natarajan, Chennai (IN); Srinivasa Raghavan Venkatachari, Chennai (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 653 days.

(21) Appl. No.: 18/223,597

(22) Filed: Jul. 19, 2023

(65) Prior Publication Data

US 2024/0028920 A1 Jan. 25, 2024

(30) Foreign Application Priority Data

Jul. 20, 2022 (IN) ............................. 202221041590

(51) Int. Cl.
*G06N 5/022* (2023.01)
*G16H 50/30* (2018.01)

(52) U.S. Cl.
CPC ............ *G06N 5/022* (2013.01); *G16H 50/30* (2018.01)

(58) Field of Classification Search
CPC .......... G06N 5/022; G06N 7/01; G06N 20/00; G16H 50/30
See application file for complete search history.

(56) References Cited

U.S. PATENT DOCUMENTS 10,726,338 B2 * 7/2020 Byron ...................... G06N 5/02
2021/0202055 A1 * 7/2021 Xiao ........................ G06N 7/01
2022/0310083 A1 * 9/2022 Mohanty ................ G10L 15/22

OTHER PUBLICATIONS

Cipresso, "Modeling behavior dynamics using computational psychometrics within virtual worlds," Frontiers in Psychology, 6 (2015).
Hartmann et al., "Model-Driven Analytics: Connecting Data, Domain Knowledge, and Learning," (2017).

(Continued)

*Primary Examiner* — Khoi V Le

(74) *Attorney, Agent, or Firm* — Finnegan, Henderson, Farabow, Garrett & Dunner, LLP

(57) ABSTRACT

This disclosure relates generally to methods and systems for deriving a behavior knowledge model for data analytics. The current automated technical solutions for monitoring the health status or behavior pattern, that apply a domain knowledge for the data analytics are very limited. Hence the conventional techniques for monitoring the health status or behavior pattern are manual, application centric and inaccurate. The present disclosure automatically leverages relevant domain knowledge and the sensor data for building a behavior knowledge model which further enhanced by the deviations identified using a machine leaning model. The present disclosure facilitates development a knowledge-driven simulator that generates sensor data sets for typical resident behavior, based on definable activity patterns and pattern influencers of interest (e.g., diabetes, nocturia).

12 Claims, 3 Drawing Sheets

(56) References Cited

OTHER PUBLICATIONS

Kibira et al., "Integrating Data Analytics and Simulation Methods to Support Manufacturing Decision Making," Proc Winter Simul Conf (2015).
"Machine Learning in Network Modeling and Simulation," National Institute of Standards and Technology (2021).
Marino et al., "Combining Physics-Based Domain Knowledge and Machine Learning using Variational Gaussian Processes with Explicit Linear Prior," (2019).
Song et al., "Individual Behavior Simulation Based on Grid Object and Agent Model," ISPRS Int. J. Geo-Inf., 8 (2019).
Von Rueden et al., "Combining Machine Learning and Simulation to a Hybrid Modelling Approach: Current and Future Directions," (2020).

* cited by examiner

METHODS AND SYSTEMS FOR DERIVING A BEHAVIOR KNOWLEDGE MODEL FOR DATA ANALYTICS

PRIORITY CLAIM

This U.S. patent application claims priority under 35 U.S.C. § 119 to: Indian Patent Application No. 202221041590, filed on Jul. 20, 2022. The entire contents of the aforementioned application are incorporated herein by reference.

TECHNICAL FIELD

The disclosure herein generally relates to the field of behavior monitoring of a person, and more specifically to methods and systems for deriving a behavior knowledge model for data analytics.

BACKGROUND

Monitoring health status or behavior pattern (for example, diabetes, nocturia eta) of a subject, such as an elderly resident, in an assisted living facilities has gained much importance over decades. Most of the current techniques in the art for monitoring the health status or behavior pattern make use of sensor data captured from a sensor network installed in the assisted living facilities. Analyzing the sensor data manually is tedious, time taking and error prone. In the recent past, analyzing the sensor data automatically referred as data analytics has been utilized for monitoring the health status or behavior pattern. However, most of the conventional approaches to such data analytics involves human using domain knowledge, either to design the data analytics approach or to select the right features from the sensor data for developing machine learning algorithms. Again, these conventional approaches are tedious, time taking and error prone due to manual operations. Moreover, acquiring sufficient data to train the machine learning algorithms is often challenging.

Further, the existing machine learning algorithm-based techniques for monitoring the health status or behavior pattern are application centric and as each time if there is a change either in the configuration and characteristics of the sensor network. For example, applying the algorithms to elderly people with different habits or living in a different environment or in the different sensor network altogether, for example. the sensor types involved, algorithms need to be modified or retrained and, in some cases, re-designed, and so on. Also, the automated technical solutions for monitoring the health status or behavior pattern, that apply a domain knowledge for the data analytics are very limited. Hence the conventional techniques for monitoring the health status or behavior pattern are manual, application centric and error prone.

SUMMARY

Embodiments of the present disclosure present technological improvements as solutions to one or more of the above-mentioned technical problems recognized by the inventors in conventional systems.

In an aspect, a processor-implemented method for deriving a behavior knowledge model for data analytics is provided. The method including the steps of: building an initial behavior knowledge model associated with one or more behaviors of a subject to be monitored, using (i) domain knowledge associated with the one or more behaviors, and (ii) a historical real-world data obtained from actual monitoring of the subject; simulating the initial behavior knowledge model, with a set of randomized occurrence patterns of events that produce the one or more behaviors, to obtain a time-series training data; transforming the time-series training data, to obtain a feature engineered training data, wherein the feature engineered training data is associated with the one or more behaviors; training a machine learning (ML) model with the feature engineered training data, to obtain a trained ML model for the one or more behaviors; applying the trained ML model on a real-world data, to predict an outcome data relevant to the one or more behaviors; determining one or more deviations in the initial behavior knowledge model, by comparing the time-series training data, the real-world data, and the outcome data; and fine-tuning the initial behavior knowledge model with the determined one or more deviations, to derive a behavior knowledge model.

In another aspect, a system for deriving a behavior knowledge model for data analytics is provided. The system includes: a memory storing instructions; one or more Input/Output (I/O) interfaces; and one or more hardware processors coupled to the memory via the one or more I/O interfaces, wherein the one or more hardware processors are configured by the instructions to; build an initial behavior knowledge model associated with one or more behaviors of a subject to be monitored, using (i) a domain knowledge associated with the one or more behaviors, and (ii) a historical real-world data obtained from actual monitoring of the subject; simulate the initial behavior knowledge model, with a set of randomized occurrence patterns of events that produce the one or more behaviors, to obtain a time-series training data; transform the time-series training data, to obtain a feature engineered training data, wherein the feature engineered training data is associated with the one or more behaviors; train a machine learning (ML) model with the feature engineered training data, to obtain a trained ML model for the one or more behaviors; apply the trained ML model on a real-world data, to predict an outcome data relevant to the one or more behaviors; determine one or more deviations in the initial behavior knowledge model, by comparing the time-series training data, the real-world data, and the outcome data; and fine-tune the initial behavior knowledge model with the determined one or more deviations determined, to derive a behavior knowledge model.

In yet another aspect, there are provided one or more non-transitory machine-readable information storage mediums comprising one or more instructions which when executed by one or more hardware processors cause: budding an initial behavior knowledge model associated with one or more behaviors of a subject to be monitored, using (i) a domain knowledge associated with the one or more behaviors, and (ii) a historical real-world data obtained from actual monitoring of the subject; simulating the initial behavior knowledge model, with a set of randomized occurrence patterns of events that produce the one or more behaviors, to obtain a time-series training data; transforming the time-series training data, to obtain a feature engineered training data, wherein the feature engineered training data is associated with the one or more behaviors; training a machine learning (ML) model with the feature engineered training data, to obtain a trained ML model for the one or more behaviors; applying the trained ML model on a real-world data, to predict an outcome data relevant to the one or more behaviors; determining one or more deviations in the initial behavior knowledge model, by comparing the time-series training data, the real-world data, and the outcome data; and fine-tuning the initial behavior knowledge model with the determined one or more deviations determined, to derive a behavior knowledge model.

In an embodiment, fine-tuning the initial behavior knowledge model with the one or more deviations, is performed until the time-series training data arising out of the behavior knowledge model is dose to the real-world data.

In an embodiment, the historical real-world data and the real-world data, are obtained from a sensor network installed in an environment of the subject to be monitored.

In an embodiment, the initial behavior knowledge model associated with the one or more behaviors of the subject to be monitored, using (i) the domain knowledge, and (ii) the historical real-world data, is built by: identifying the one or more behaviors of interest associated with the subject to be monitored; determining a range of variations associated with each of the one or more behaviors, using (i) the domain knowledge, and (ii) the historical real-world data; identifying one or more visible signs associated with each of the one or ore behaviors, using the domain knowledge; incorporating one or more structures and one or more processes that produce the one or more behaviors and the associated one or more visible signs, using the domain knowledge; adding (i) one or more process parameters associated with each process of the one or more processes, (ii) one or more occurrence patterns of events that trigger the one or more processes, and (iii) one or more relationships between characteristics of the one or more structures and the one or more behaviors; and determining values and coefficients associated with (i) the one or more process parameters, (ii) the one or more occurrence patterns, and (iii) one or more relationships, by reverse engineering the historical real-world data.

In an embodiment, a structure of the one or more structures, is an adjacency data of the environment in which the subject to be monitored; and a process of the one or more processes is a traversal data determined based on the corresponding structure.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

The present disclosure solves the technical problems in the art for deriving a behavior knowledge model for data analytics, for monitoring the health status or behavior pattern (for example, diabetes, nocturia etc.) of a subject. The present disclosure automatically leverages relevant domain knowledge and the sensor data for building a behavior knowledge model which further enhanced by the deviations identified using a machine leaning model. The present disclosure facilitates development a knowledge-driven simulator that generates sensor data sets for typical resident behavior, based on definable activity patterns and pattern influencers of interest (e.g., diabetes, nocturia).

Figure 1:
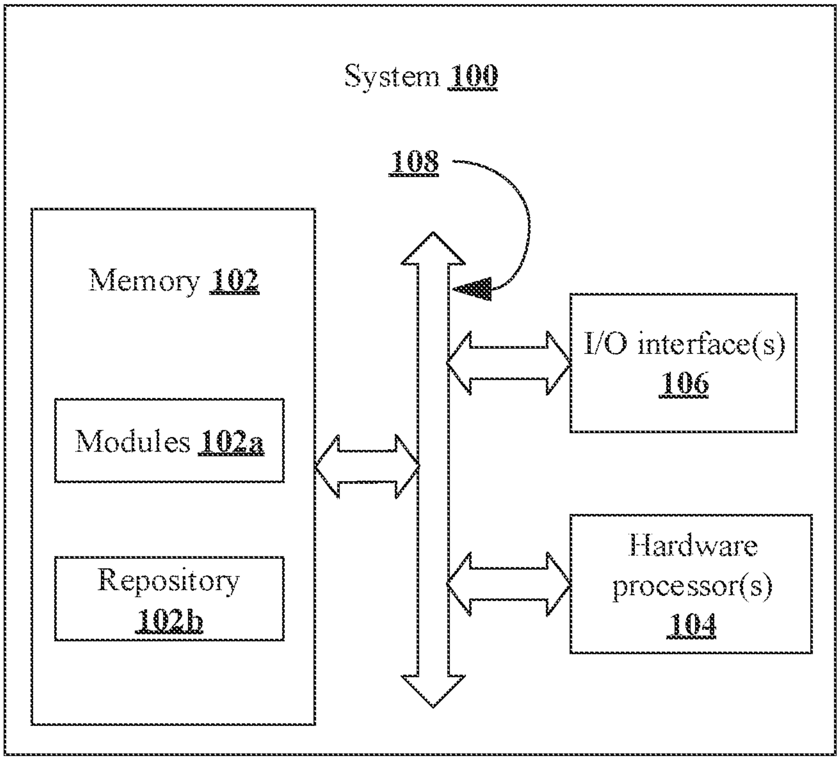
FIG. 1 is an exemplary block diagram of a system for deriving a behavior knowledge model for data analytics, in accordance with some embodiments of the present disclosure.
Figure 2:
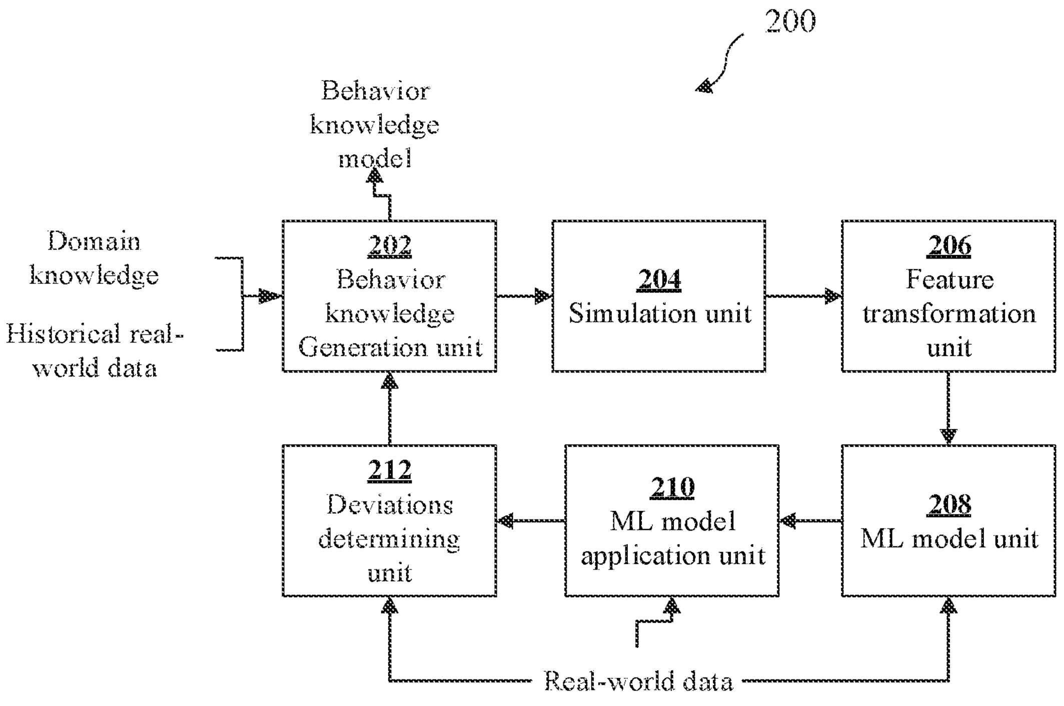
FIG. 2 is an exemplary block diagram illustrating modules of the system of FIG. 1 for deriving the behavior knowledge model for data analytics, in accordance with some embodiments of the present disclosure.
Figure 3:
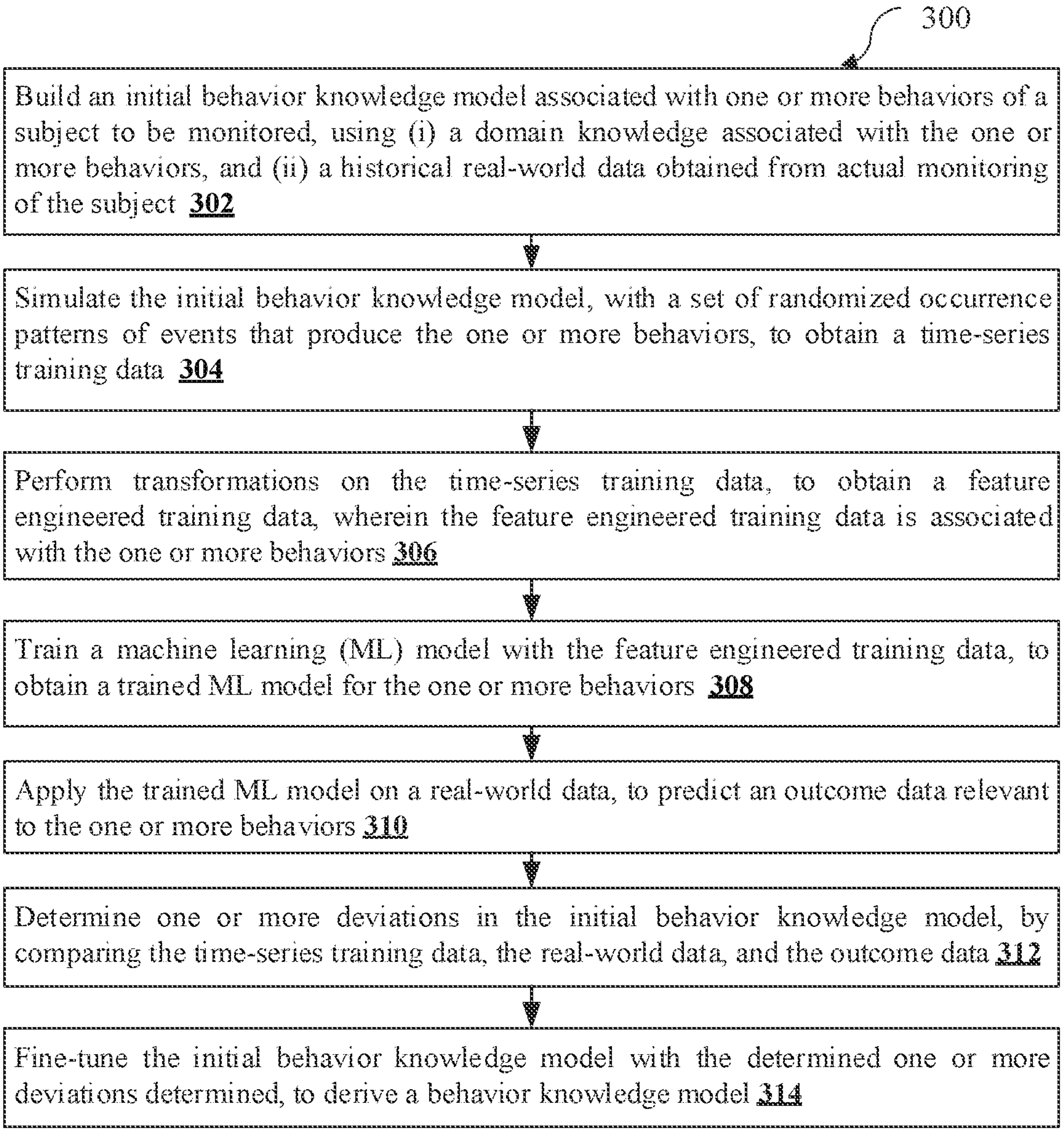
FIG. 3 illustrates exemplary flow diagram of a processor-implemented method for deriving the behavior knowledge model for data analytics, in accordance with some embodiments of the present disclosure.

Referring now to the drawings, and more particularly to FIG. 1 through FIG. 3, where similar reference characters denote corresponding features consistently throughout the figures, there are shown preferred embodiments and these embodiments are described in the context of the following exemplary systems and/or methods.

FIG. 1 is an exemplary block diagram of a system 100 for deriving a behavior knowledge model for data analytics, in accordance with some embodiments of the present disclosure. In an embodiment, the system 100 includes or is otherwise in communication with one or more hardware processors 104, communication interface device(s) or input/output (I/O) interface(s) 106, and one or more data storage devices or memory 102 operatively coupled to the one or more hardware processors 104. The one or more hardware processors 104, the memory 102, and the I/O interface(s) 106 may be coupled to a system bus 108 or a similar mechanism.

The I/O interface(s) 106 may include a variety of software and hardware interfaces, for example, a web interface, a graphical user interface, and the like. The I/O interface(s) 106 may include a variety of software and hardware interfaces, for example, interfaces for peripheral device(s), such as a keyboard, a mouse, an external memory, a plurality of sensor devices, a printer and the like. Further, the I/O interface(s) 106 may enable the system 100 to communicate with other devices, such as web servers and external databases.

The I/O interface(s) 106 can facilitate multiple communications within a wide variety of networks and protocol types, including wired networks, for example, local area network (LAN), cable, etc., and wireless networks, such as Wireless LAN (WLAN), cellular, or satellite. For the purpose, the I/O interface(s) 106 may include one or more ports for connecting a number of computing systems with one another or to another server computer. Further, the I/O interface(s) 106 may include one or more ports for connecting a number of devices to one another or to another server.

The one or more hardware processors 104 may be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 are configured to fetch and execute computer-readable instructions stored in the memory 102. In the context of the present disclosure, the expressions 'processors' and 'hardware processors' may be used interchangeably. In an embodiment, the system 100 can be implemented in a variety of computing systems, such as laptop computers, portable computers, notebooks, hand-held devices, workstations, mainframe computers, servers, a network cloud and the like.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 102 includes a plurality of modules 102*a* and a repository 102*b* for storing data processed, received, and generated by one or more of the plurality of modules 102*a*. The plurality of modules 102*a* may include routines, programs, objects, components, data structures, and so on, which perform particular tasks or implement particular abstract data types.

The plurality of modules 102*a* may include programs or computer readable instructions or coded instructions that supplement applications or functions performed by the system 100. The plurality of modules 102*a* may also be used as, signal processor(s), state machine(s), logic circuitries, and/or any other device or component that manipulates signals based on operational instructions. Further, the plurality of modules 102*a* can be used by hardware, by computer-readable instructions executed by the one or more hardware processors 104, or by a combination thereof. In an embodiment, the plurality of modules 102*a* can include various sub-modules (not shown in FIG. 1). Further, the memory 102 may include information pertaining to input(s)/output(s) of each step performed by the processor(s) 104 of the system 100 and methods of the present disclosure.

The repository 102*b* may include a database or a data engine. Further, the repository 102*b* amongst other things, may serve as a database or includes a plurality of databases for storing the data that is processed, received, or generated as a result of the execution of the plurality of modules 102*a*. Although the repository 102*b* is shown internal to the system 100, it will be noted that, in alternate embodiments, the repository 102*b* can also be implemented external to the system 100, where the repository 102*b* may be stored within an external database (not shown in FIG. 1) communicatively coupled to the system 100. The data contained within such external database may be periodically updated. For example, data may be added into the external database and/or existing data may be modified and/or non-useful data may be deleted from the external database. In one example, the data may be stored in an external system, such as a Lightweight Directory Access Protocol (LDAP) directory and a Relational Database Management System (RDBMS). In another embodiment, the data stored in the repository 102*b* may be distributed between the system 100 and the external database.

Referring collectively to FIG. 2 and FIG. 3, components and functionalities of the system 100 are described in accordance with an example embodiment of the present disclosure. For example, FIG. 2 is an exemplary block diagram illustrating modules 200 of the system 100 of FIG. 1 for deriving the behavior knowledge model for data analytics, in accordance with some embodiments of the present disclosure. As shown in FIG. 2, the modules 200 includes a behavior knowledge generation unit 202, a simulation unit 204, a feature transformation unit 206, a machine learning (ML) model unit 208, an ML model application unit 210, and a deviations determining unit 212. In an embodiment, the modules 200 of FIG. 2 may be stored in the plurality of modules 102*a* comprised in the memory 102 of the system 100.

FIG. 3 illustrates exemplary flow diagram of a processor-implemented method 300 for deriving the behavior knowledge model for data analytics, in accordance with some embodiments of the present disclosure. Although steps of the method 300 including process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any practical order. Further, some steps may be performed simultaneously, or some steps may be performed alone or independently.

At step 302 of the method 300, the one or more hardware processors 104 of the system 100 are configured to build an initial behavior knowledge model using domain knowledge and a historical real-world data. The behavior knowledge generation unit 202 includes the mechanics to build the initial behavior knowledge model using domain knowledge and a historical real-world data. The initial behavior knowledge model is associated with one or more behaviors of a subject to be monitored. In an embodiment, the one or more behaviors of the subject such as cooking, watching TV, spending more time in washroom or more urinating, less sleeping, unable to walk, and so on. The one or more behaviors are based and associated the activities or events performed by the subject in day-to-day life in a given environment. In an embodiment, the given environment includes a house, residence, office, hospital, day care residence, and so on, and the combination thereof. In an embodiment, the subject includes but are not limited to an elderly person, a disabled person, a person having health complications (ill person), a person whose health to be monitored, a person whose daily life to be monitored, and any other person whose behavior to be monitored.

Hence the domain knowledge is associated with the one or more behaviors in general. In an embodiment, the domain knowledge is received from domain knowledge sources, domain experts, general facts, and a combination thereof and transformed into a standard structure model such as a knowledge repository, knowledge graph, and so on, having the one or more behaviors, definition of each behavior, relationship between two or more behaviors and so on.

The historical real-world data is associated with monitoring of the subject and includes the one or more activities or events done by the subject in the past and such data includes the one or more activities performed along with the time-stamps, time spent for each activity, a sequence or a pattern of the activities, and so on. In an embodiment, the historical real-world data is obtained from a sensor network installed in the given environment of the subject. In an embodiment, the sensor network includes an image sensor, an infrared sensor, an audio sensor, a video sensor, or a combination thereof.

Building the initial behavior knowledge model using the domain knowledge and the historical real-world data is explained in detail in the below steps. In the first step, the one or more behaviors of interest associated with the subject to be monitored, are identified. For examples, for elderly in assisted living facilities or at home with the monitoring sensor network installed, the behavior of interest may be their regular pattern of activities consisting of waking up, brushing teeth, using bathroom, cooking etc. In the second step, a range of variations associated with each of the one or more behaviors or interest are determined using the domain knowledge and the historical real-world data. For elderly people for example, whether they have diabetes or nocturia, whether they are unwell, whether they are socializing less and so on.

In the third step, one or more visible signs associated with each of the one or more behaviors of interest are identified using the domain knowledge. For example, people with diabetes may urinate more frequently and drink more water. Focus on the symptoms that are observable using the sensor network for example, if the behavioral characteristic of interest is whether the person has diabetes, one of the visible sign is more frequent bathroom usage. If necessary, inputs from domain experts about what normal and abnormal behavior looks like are considered.

In the fourth step, one or more structures and one or more processes that produce the one or more behaviors and the associated one or more visible signs, are incorporated using the domain knowledge. For example, going to the bathroom involves a structure of rooms with adjacency relationships between them e.g., bedroom is adjacent to kitchen, kitchen is adjacent to bathroom. Similarly, the processes involved for the same for example go from bedroom to kitchen to bathroom, use bathroom for a period of time, then return to bedroom via kitchen. Similarly, "going out of the house" may involve going to bedroom to dress up, optionally using bathroom, leaving house via living room front door, spending a period of time outside, coming back in via the front door, optionally using bathroom, going to bedroom to change clothes again.

In an embodiment, the structure of the one or more structures, is an adjacency data of the environment in which the subject to be monitored. For example, details of the adjacent rooms, things, resources and so on. In an embodiment, the process of the one or more processes is a traversal data determined based on the corresponding structure. For example, the process for going to bathroom, is the traversal data from the present position of the subject till the subject is reached to the bathroom.

The concept of structure and process are more clearly explained with the help of below definitions:

(a). An event is any occurrence of interest e.g., waking up, opening a door, taking medicine, returning from outing, leaving a room (b). An occurrence pattern indicates when an event will occur e.g.

At a fixed time

At a random distribution pattern around a fixed time e.g., Poisson distribution (7.0, 30). This indicates that the wakeup time is 7 am, with a distribution pattern around that time e.g., sometimes 6.15, sometimes 7.40 etc. The standard deviation of the distribution is 30.

Periodically ("cyclic") e.g., people go to the bathroom every 4 hours. This may also have a distribution pattern—sometimes 3.5, sometimes 5.2 hours etc.

(c). Events trigger processes e.g., breakfast event may trigger a breakfast process. The process has a process definition, which includes The duration of the process (e.g., 30 minutes, but also with some random variation)

The process may breakdown into smaller activities e.g., "breakfast" may involve cooking breakfast, eating, and washing up afterwards. This is shown by the perform sequence column.

Behavior effects specifications what happens when the process executes e.g., people move into or exit a room, spend time in a room, open or dose a medicine box etc.

In the fifth step, one or more process parameters associated with each process of the one or more processes, one or more occurrence patterns of events that trigger the one or more processes, and one or more relationships between characteristics of the one or more structures and the one or more behaviors, are added. In an embodiment, the one or more process parameters includes but are not limited to duration of the process, process, sequence of the process with events, and so on. For example, time spent in bathroom, time spent outside the house, time spent to go from one room to another, likelihood of using bathroom before and after going out, and so on.

In an embodiment, the one or more occurrence patterns of events include the occurrence patterns of such events that trigger the one or more processes. For example, waking up happens once a day, at a fixed time+/− a variable time e.g., 7 am+/−2 hours. Some activities (processes) decompose into sequential sub-processes e.g., having a meal decomposes into cook+take medicine (if any)+eat+take medicine (if any)+washup. In such cases, we only need a single occurrence pattern for the higher-level processes (e.g., have meal). The processes also have duration parameters.

In the sixth and last step, values and coefficients associated with (i) the one or more process parameters, (ii) the one or more occurrence patterns, and (iii) one or more relationships, are determined by reverse engineering the historical real-world data. Further, the values and the coefficients are also estimated based on the domain knowledge.

Basically, the historical real-world data consists of a series of sensor readings with associated timestamps. From this data, below information can be extracted:

Change events—time instants at which a sensor value changes. From this, events (e.g., entering a room) are derived as a set of sensor value changes.

Look for patterns of change events and identify higher-order events or process instances e.g., going to the bathroom involves a series of closely spaced room-entry and room-exit events, followed by room-entry into bathroom, then duration inside bathroom, then room-exit from bathroom, followed by room-entry and room-exit for other rooms, and ending in room-entry to some room. Thus, pattern specifications to recognize higher order events are created.

Processes instance occurrences are detected based on the events e.g., "use bathroom process". The duration of the process is determined based on the timestamps.

Then, the occurrence patterns and durations, including the distribution patterns of how they vary, are deduced from the detected series of events and process instances.

Table 1 shows an exemplary historical real-world data:

TABLE 1

| Location | Observation_timestamp |
|---|---|
| bedroom_master | Aug. 2, 2018 00:01 |
| bedroom_master | Aug. 2, 2018 00:11 |
| bedroom_master | Aug. 2, 2018 00:16 |
| kitchen | Aug. 2, 2018 00:20 |
| living_room | Aug. 2, 2018 00:20 |
| toilet_bathroom | Aug. 2, 2018 00:20 |
| kitchen | Aug. 2, 2018 00:24 |
| living_room | Aug. 2, 2018 00:24 |

TABLE 1-continued

| Location | Observation_timestamp |
|---|---|
| bedroom_master | Aug. 2, 2018 00:25 |
| bedroom_master | Aug. 2, 2018 01:14 |
| bedroom_master | Aug. 2, 2018 01:59 |
| bedroom_master | Aug. 2, 2018 02:22 |
| bedroom_master | Aug. 2, 2018 02:35 |
| bedroom_master | Aug. 2, 2018 02:45 |
| bedroom_master | Aug. 2, 2018 03:18 |

Hence, using the information of all the events, process instances, their durations and occurrence variation patterns, the initial behavior knowledge model is built. Furthermore, the process instances may have parameters e.g., an outing may have an outing type (e.g., in-building errand such as checking mailbox, lunch or dinner outing, shopping, extended visits elsewhere, etc.). These parameters from are derived from the process signatures, For example:

An in-building errand has a short duration e.g., less than 20 minutes

Meal outings happen at particular times of day and have durations of 30 minutes-4 hours.

Shopping trips may occur at other times of day and have similar durations. [Practically, one cannot distinguish perfectly between meal and shopping]

Extended visits may last 4 hours-several days.

Overall, the reverse engineering helps creating a series of signature specifications which are used to process sensor data, and recognize events and processes of interest, along with process parameters and associated characteristics (e.g., durations, occurrence patterns). Hence the built initial behavior knowledge model includes the following components:

What events occur

The occurrence patterns of the events

The processes triggered by the events (including sequences of subprocesses)

The durations of the process, and

The effect of the process on the historical real-world data.

How the behaviors vary with characteristics of interest e.g., whether the person has diabetes may influence how frequently they use the bathroom; when people become less social, outing occurrence frequency drops drastically; people with less mobility take longer to move across a room, and so on.

At step 304 of the method 300, the one or more hardware processors 104 of the system 100 are configured to simulate the initial behavior knowledge model built at step 302 of the method 300, to obtain a time-series training data, through the simulation unit 204. A set of software routines with a set of randomized occurrence patterns of events that produce the one or more behaviors are used while simulating the initial behavior knowledge model to obtain the time-series training data. The set of randomized occurrence patterns of events that produce the one or more behaviors of interest which to be monitored are identified in prior. The obtained time-series training data obtains all the details corresponding to the set of randomized occurrence patterns of events that produce the one or more behaviors, along with their values, the coefficients and along with the timestamps. Table 2 shows the exemplary time-series training data.

TABLE 2

| TimeOfDay | Current Location | Activity Duration | Total Duration | ActivityName |
|---|---|---|---|---|
| Aug. 2, 2018 00:01 | Bedroom | 581 | 1108 | Rest.Bedroom |
| Aug. 2, 2018 00:20 | Kitchen | 0 | 0 | MoveTo.Kitchen |
| Aug. 2, 2018 00:20 | LivingRoom | 36 | 36 | MoveTo.LivingRoom |
| Aug. 2, 2018 00:20 | Bathroom | 211 | 211 | UseBathroom.One |
| Aug. 2, 2018 00:24 | Kitchen | 21 | 21 | MoveTo.Kitchen |
| Aug. 2, 2018 00:24 | LivingRoom | 64 | 64 | MoveTo.LivingRoom |
| Aug. 2, 2018 00:25 | Bedroom | 2929 | 12738 | Sleep.Bedroom |
| Aug. 2, 2018 03:58 | LivingRoom | 0 | 0 | MoveTo.LivingRoom |
| Aug. 2, 2018 03:58 | Kitchen | 21 | 21 | MoveTo.Kitchen |
| Aug. 2, 2018 03:58 | Bathroom | 207 | 207 | UseBathroom.One |
| Aug. 2, 2018 04:01 | Bedroom | 497 | 11068 | Sleep.Bedroom |
| Aug. 2, 2018 07:06 | LivingRoom | 1 | 1 | MoveTo.LivingRoom |
| Aug. 2, 2018 07:06 | Kitchen | 34 | 34 | MoveTo.Kitchen |
| Aug. 2, 2018 07:06 | Bathroom | 198 | 198 | UseBathroom.One |
| Aug. 2, 2018 07:10 | Bedroom | 808 | 808 | Errand.Bedroom |
| Aug. 2, 2018 07:23 | LivingRoom | 18 | 18 | MoveTo.LivingRoom |
| Aug. 2, 2018 07:24 | Kitchen | 76 | 76 | MoveTo.Kitchen |
| Aug. 2, 2018 07:25 | Bathroom | 454 | 454 | UseBathroom.Wash |
| Aug. 2, 2018 07:32 | Kitchen | 7 | 7 | Errand.Kitchen |
| Aug. 2, 2018 07:33 | Bathroom | 419 | 419 | UseBathroom.Wash |
| Aug. 2, 2018 07:39 | LivingRoom | 66 | 66 | Errand.LivingRoom |
| Aug. 2, 2018 07:41 | Bathroom | 384 | 384 | UseBathroom.Wash |
| Aug. 2, 2018 07:47 | Kitchen | 238 | 238 | Errand.Kitchen |
| Aug. 2, 2018 07:51 | LivingRoom | 3 | 3 | MoveTo.LivingRoom |
| Aug. 2, 2018 07:51 | Bedroom | 190 | 190 | Errand.Bedroom |
| Aug. 2, 2018 07:54 | Bathroom | 350 | 491 | UseBathroom.Wash |
| Aug. 2, 2018 08:02 | LivingRoom | 197 | 197 | Errand.LivingRoom |
| Aug. 2, 2018 08:06 | Bedroom | 105 | 105 | Errand.Bedroom |
| Aug. 2, 2018 08:07 | Door | 56 | 56 | Errand.Door |
| Aug. 2, 2018 08:08 | LivingRoom | 673 | 673 | Errand.LivingRoom |
| Aug. 2, 2018 08:20 | Bathroom | 805 | 805 | UseBathroom.Wash |
| Aug. 2, 2018 08:33 | Kitchen | 240 | 240 | Errand.Kitchen |
| Aug. 2, 2018 08:37 | LivingRoom | 99 | 99 | Errand.LivingRoom |
| Aug. 2, 2018 08:39 | Bathroom | 315 | 315 | UseBathroom.Wash |
| Aug. 2, 2018 08:44 | LivingRoom | 4 | 4 | MoveTo.LivingRoom |
| Aug. 2, 2018 08:44 | Bedroom | 1027 | 1027 | Rest.Bedroom |
| Aug. 2, 2018 09:01 | Kitchen | 182 | 182 | Errand.Kitchen |

The obtained time-series training data at step 304 is raw, non-streamlined data and includes all the data corresponding to the set of randomized occurrence patterns of events that produce the one or more behaviors. However, the only the behaviors that are of interest and corresponding occurrence patterns of events to be filtered out. Hence at step 306 of the method 300, the one or more hardware processors 104 of the system 100 are configured to transform the time-series training data obtained at step 304 of the method, to obtain a feature engineered training data. The feature transformation unit 206 includes the feature recommendation engine and the data filtering techniques to apply the feature engineering in the way of transformation and data filtering on the obtained time-series training data to obtain the feature engineered training data.

The resulted feature engineered training data is only associated with the one or more behaviors of interest of the subject to be monitored for. Further, resulted feature engineered training data is formed in accordance with the behavior as output variable and the associated occurrence patterns of events are input variables. The output variable (the behavior) is dependent on the one or more input variables (the occurrence patterns of events), and hence the resulted feature engineered training data is structured and suitable for training a machine learning (ML) model.

At step 308 of the method 300, the one or more hardware processors 104 of the system 100 are configured to train the machine learning (ML) model with the feature engineered training data obtained at step 306 of the method 300, to obtain a trained ML model. The obtained trained ML model is associated with the one or more behaviors for which the feature engineered training data is corresponding to. In an embodiment, the feature engineered training data is divided into a training data and a validation data based on a predefined ratio. In an embodiment, the predefined ratio is 80%:20%. For example, if the feature engineered training data contains 100 samples, then the training data contains 80 samples and the validation data includes 20 samples. Hence the ML model is first trained with the training data and then validated with the validation data, before obtaining the trained ML model.

In an embodiment, the machine learning (ML) model may be a classification model, or a regression model based on the nature of the feature engineered training data. In an embodiment, the machine learning (ML) is one of: a random forest model, support vector machine (SVM), a decision tree, a logistic regression, a gradient boost model, and so on. In an embodiment, the machine learning (ML) model unit 208 includes different number of machine learning models such as classification models and regression models, out of which a suitable ML is selected based on the feature engineered training data. The trained model is capable of detecting the one or more behaviors based on the occurrence patterns of events.

At step 310 of the method 300, the one or more hardware processors 104 of the system 100 are configured to train a apply the trained ML model obtained at step 308 of the method 300 on a real-world data, to predict an outcome data relevant to the one or more behaviors or behavioral characteristics such as diabetes. The ML model application unit 210, applies the trained ML model to the environment, where the subject to be monitored with the help of real-world data of such environment. More detail, the outcome data includes the one or more behaviors based on the occurrence patterns of events present in the real-world data.

In an embodiment, the real-world data is the actual data based on which the subject to be monitored for identifying the one or more behaviors. In an embodiment, the real-world data includes the one or more activities or events done by the subject and such data includes the one or more activities performed along with the timestamps, time spent for each activity, a sequence or a pattern of the activities, and so on. In an embodiment, the real-world data is obtained from the sensor network installed in the given environment of the subject. In an embodiment, the sensor network includes the image sensor, the infrared sensor, the audio sensor, the video sensor, or a combination thereof.

At step 312 of the method 300, the one or more hardware processors 104 of the system 100 are configured to determine one or more deviations in the initial behavior knowledge model, through the deviations determining unit 212. The one or more deviations in the initial behavior knowledge model are determined by comparing the time-series training data obtained at step 304 of the method 300, with the real-world data mentioned at step 310 of the method 300, and possibly also determining whether the real-world data is consistent with the outcome data obtained at step 310 of the method 300. The one or more deviations are associated with deviations of the one or more activities or events, the occurrence patterns of events and the corresponding behaviors.

For example, the behavior knowledge model may include outings related data of the subject being monitored in last several hours, say 2-12 hours. But real-world data may show some outings related data that last 48 hours or more. This is detected as a deviation in maximum duration of the outing data. In this case, a new type of activity "TripOuting" which lasts multiple days is included as a result of the identified deviation.

In one more example, the behavior knowledge model may show a maximum of 2 Room Transit events occurring together e.g., Transit from Bedroom to Kitchen, and Kitchen to Bathroom. However, the real-world data may show some instances of 10 or 12 Room Transit events occurring together i.e., Bedroom to Kitchen to Living Room to Kitchen to Bedroom to Kitchen to Bedroom. This may be detected as a difference in occurrence patterns of Room Transit events between the behavior knowledge simulation and the real-world data. Alternatively, it may be detected as a gap in the outcome data. The trained M model may not be able to assign any activity label to the event sequence. This deviation is communicated to the domain expert, who may then identify this as a new abnormal behavior that needs to be recognized. That new behavior is then added manually to the behavior knowledge model.

The basic idea for identifying the one or more deviations is to compare the time-series training data obtained at step 304 of the method 300, with the real-world data mentioned at step 310 of the method 300, and possibly also utilizing the outcome data obtained at step 310 of the method 300. The comparison includes:

- Frequency of changes in sensor values
- Correlations between sensor values
- Maximum, minimum, mean, standard deviation etc. of parameter values derived from the sensor values e.g., durations, occurrence counts, occurrence timing
- Sequence of actions involved in process instances and how they vary. For example, if a Meal involves cooking+eating+washing up, then how the durations and even ordering of each subprocess vary in the simulation and the real world are compared The deviations analysis may show various types of deviations including:

- Changes in behavior specifications e.g., durations, occurrence patterns etc. These become minor adjustments to the initial behavior knowledge model.
- Missed phenomena. For example, the time-series training data may show that outings last at most a few hours only. But real-world data may show that some outings last several days. Based on this, a particular outing type "outstation trip" may have been missed out will be identified.
- Changes to process sequences. For example, some meals may not be followed by washing up at all. Or there may be a long-time lag between cooking and eating, which may not be allowed at all in the simulation. These become significant changes to the initial behavior knowledge model. This helps to identify the precise gap in the initial behavior knowledge model and the fix required—deviation analysis simply shows that the time-series training data contains only particular patterns, while real-world data shows other patterns which never occur in time-series training data.

At step 314 of the method 300, the one or more hardware processors 104 of the system 100 are configured to fine-tune the initial behavior knowledge model with the determined one or more deviations at step 312 of the method, to derive a behavior knowledge model. The process of fine-tuning the initial behavior knowledge model with the one or more deviations, is performed until the time-series training data arising out of the behavior knowledge model is close to the real-world data. In other words, the steps 304 through 314 of the method 300 are continuously performed until the time-series training data arising out of the behavior knowledge model is dose to the real-world data.

In other words, the steps 304 through 312 of the method 300 are repeated sequentially considering the behavior knowledge model as the initial behavior knowledge model, until the time-series training data arising out of the behavior knowledge model is dose to the real-world data. The final obtained behavior knowledge model is the final model used for the end-applications for monitoring the subject to identify one or more behaviors of the subject interested in and responding to those behaviors of interest either with automated actions or human interventions, as appropriate to the end-application.

The behavior knowledge model is bunt using both the sensor data and the domain knowledge and the behavior knowledge model is built automatically. The behavior knowledge model is enhanced and tuned further with the use of deviations identified from the trained ML model and the real-time data. Hence the behavior knowledge model can be tuned to actual real-world situation in less time without any manual intervention or minimal manual intervention. The behavior knowledge model is enhanced till the performance is close to the real-world data, hence the enhanced behavior knowledge model is accurate for the particular real-world situation of interest. The concept of such a behavior knowledge model is not any application centric and algorithm centric and can be applied in any configurations and application area. Though the main application of the present invention is for monitoring the health status or behavior pattern (for example, diabetes, nocturia etc.) of the elderly resident, in an assisted living facilities, the scope of the invention is not limited to monitoring mental status of a healthy people, children, where the application domain is relevant.

The method and systems of the present disclosure provides an automated approach for adapting the data analytics solution to a new real-world situation and in the given environment. For example, if the assisted living solution is to be deployed in a different country where the elderly person having different living habits and pattern of activities, and the physical facilities include a different set of sensors, the present disclosure provides an automated approach to identifying the deviations and fine-tuning the previous behavior knowledge model to reflect the new situation, activity pattern and physical facilities. This reduces both the effort and cycle-time needed to develop the data analytics solution for the new environment.

The method and systems of the present disclosure provides an automated approach to apply domain knowledge for data analytics, as well as fine-tuning the domain knowledge to the details of particular real-world situations, given the observation sensory data. Further, the present disclosure provides the automated approach to apply knowledge of the data gathering facilities, including sensor configurations and characteristics, for solving the problem of data analytics, particularly for data cleansing (which is necessary even if machine learning is used). The present invention provides a dynamic technique with reduced or no dependency on the domain experts and improves productivity and cycle time for algorithm development and adaptation.

The embodiments of present disclosure herein address unresolved problem of deriving the behavior knowledge model for data analytics, used for monitoring the health status or behavior pattern (for example, diabetes, nocturia etc.) of the subject. The present disclosure automatically leverages relevant domain knowledge and the sensor data for building a behavior knowledge model which further enhanced by the deviations identified using a machine leaning model. The present disclosure facilitates development a knowledge-driven simulator that generates sensor data sets for typical resident behavior, based on definable activity patterns and pattern influencers of interest (e.g., diabetes, nocturia).

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be, hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional budding blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context dearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor-implemented method for deriving a behavior knowledge model for data analytics, comprising the steps of:

building, via one or more hardware processors, an initial behavior knowledge model associated with one or more behaviors of a subject to be monitored, using (i) domain knowledge associated with the one or more behaviors, and (ii) a historical real-world data obtained from actual monitoring of the subject, wherein (i) the historical real-world data and (ii) the real-world data, are obtained from sensor network installed in an environment of the subject to be monitored, and the sensor network includes an image sensor, an infrared sensor, an audio sensor, a video sensor, or a combination thereof;

simulating, via the one or more hardware processors, the initial behavior knowledge model, with a set of randomized occurrence patterns of events that produce the one or more behaviors, to obtain a time-series training data, and with development of a knowledge-driven simulator, sensor data sets are generated for typical resident behavior, in accordance with definable activity patterns and pattern influencers of interest;

transforming, via the one or more hardware processors, the time-series training data, to obtain a feature engineered training data, wherein the feature engineered training data is associated with the one or more behaviors;

training, via the one or more hardware processors, a machine learning (ML) model with the feature engineered training data, to obtain a trained ML model for the one or more behaviors;

applying, via the one or more hardware processors, the trained ML model on a real-world data, to predict an outcome data relevant to the one or more behaviors;

determining via the one or more hardware processors, one or more deviations in the initial behavior knowledge model, by comparing the time-series training data, the real-world data, and the outcome data;

fine-tuning, via the one or more hardware processors, the initial behavior knowledge model with the determined one or more deviations by iterating steps of simulating, transforming, training, applying and determining until time-series training data matches the real-world data, to derive a behavior knowledge model; and monitoring, by the derived behavior knowledge model, the subject to identify the behaviors of the subject and respond to the behaviors with automated actions as appropriate to an end-application, wherein the derived behavior knowledge model is independent of the end-application or algorithm and reusable in varied configurations and application area.

2. The method of claim 1, wherein fine-tuning the initial behavior knowledge model with the one or more deviations, is performed until the time-series training data arising out of the behavior knowledge model is close to the real-world data.

3. The method of claim 1, wherein building the initial behavior knowledge model associated with the one or more behaviors of the subject to be monitored, using (i) the domain knowledge, and (ii) the historical real-world data, comprises:

identifying the one or more behaviors of interest associated with the subject to be monitored;

determining a range of variations associated with each of the one or more behaviors, using (i) the domain knowledge, and (ii) the historical real-world data;

identifying one or more visible signs associated with each of the one or more behaviors, using the domain knowledge;

incorporating one or more structures and one or more processes that produce the one or more behaviors and the associated one or more visible signs, using the domain knowledge;

adding (i) one or more process parameters associated with each process of the one or more processes, (ii) one or more occurrence patterns of events that trigger the one or more processes, and (iii) one or more relationships between characteristics of the one or more structures and the one or more behaviors; and determining values and coefficients associated with (i) the one or more process parameters, (ii) the one or more occurrence patterns, and (iii) one or more relationships, by reverse engineering the historical real-world data, wherein the reverse engineering creates a series of signature specifications to process sensor data, recognize events and processes of interest, along with process parameters and associated characteristics such as durations, and occurrence patterns.

4. The method of claim 3, wherein:

(i) a structure of the one or more structures, is an adjacency data of the environment in which the subject to be monitored; and (ii) a process of the one or more processes is a traversal data determined based on the corresponding structure.

5. A system for deriving a behavior knowledge model for data analytics, comprising:

a memory storing instructions;

one or more input/output (I/O) interfaces; and one or more hardware processors coupled to the memory via the one or more I/O interfaces, wherein the one or more hardware processors are configured by the instructions to:

build an initial behavior knowledge model associated with one or more behaviors of a subject to be monitored, using (i) a domain knowledge associated with the one or more behaviors, and (ii) a historical real-world data obtained from actual monitoring of the subject, wherein (i) the historical real-world data and (ii) the real-world data, are obtained from sensor network installed in an environment of the subject to be monitored, and the sensor network includes an image sensor, an infrared sensor, an audio sensor, a video sensor, or a combination thereof;

simulate the initial behavior knowledge model, with a set of randomized occurrence patterns of events that produce the one or more behaviors, to obtain a time-series training data, and with development of a knowledge-driven simulator, sensor data sets are generated for typical resident behavior, in accordance with definable activity patterns and pattern influencers of interest;

transform the time-series training data, to obtain a feature engineered training data, wherein the feature engineered training data is associated with the one or more behaviors;

train a machine learning (ML) model with the feature engineered training data, to obtain a trained ML model for the one or more behaviors;

apply the trained ML model on a real-world data, to predict an outcome data relevant to the one or more behaviors;

determine one or more deviations in the initial behavior knowledge model, by comparing the time-series training data, the real-world data, and the outcome data;

fine-tune the initial behavior knowledge model with the determined one or more deviations determined by iterating steps of simulating, transforming, training, applying and determining until time-series training data matches the real-world data, to derive a behavior knowledge model; and monitor, by the derived behavior knowledge model, the subject to identify the behaviors of the subject and respond to the behaviors with automated actions as appropriate to an end-application, wherein the derived behavior knowledge model is independent of the end-application or algorithm and reusable in varied configurations and application area.

6. The system of claim 5, wherein the one or more hardware processors are configured to fine-tune the initial behavior knowledge model with the one or more deviations, until the time-series training data arising out of the behavior knowledge model is close to the real-world data.

7. The system of claim 5, wherein the one or more hardware processors are configured to build the initial behavior knowledge model associated with the one or more behaviors of the subject to be monitored, using (i) the domain knowledge, and (ii) the historical real-world data, by identifying the one or more behaviors of interest associated with the subject to be monitored;

determining a range of variations associated with each of the one or more behaviors, using (i) the domain knowledge, and (ii) the historical real-world data;

identifying one or more visible signs associated with each of the one or more behaviors, using the domain knowledge;

incorporating one or more structures and one or ore processes that produce the one or more behaviors and the associated one or more visible signs, using the domain knowledge;

adding (i) one or more process parameters associated with each process of the one or more processes, (ii) one or more occurrence patterns of events that trigger the one or more processes, and (iii) one or more relationships between characteristics of the one or more structures and the one or more behaviors; and determining values and coefficients associated with (i) the one or more process parameters, (ii) the one or more occurrence patterns, and (iii) one or more relationships, by reverse engineering the historical real-world data, wherein the reverse engineering creates a series of signature specifications to process sensor data, recognize events and processes of interest, along with process parameters and associated characteristics such as durations, and occurrence patterns.

8. The system of claim 7, wherein:

(i) a structure of the one or more structures, is an adjacency data of the environment in which the subject to be monitored; and (ii) a process of the one or more processes is a traversal data determined based on the corresponding structure.

9. One or more non-transitory machine-readable information storage mediums comprising one or more instructions which when executed by one or more hardware processors cause:

building, an initial behavior knowledge model associated with one or more behaviors of a subject to be monitored, using (i) domain knowledge associated with the one or more behaviors, and (ii) a historical real-world data obtained from actual monitoring of the subject, wherein (i) the historical real-world data and (ii) the real-world data, are obtained from sensor network installed in an environment of the subject to be monitored, and the sensor network includes an image sensor, an infrared sensor, an audio sensor, a video sensor, or a combination thereof;

simulating, the initial behavior knowledge model, with a set of randomized occurrence patterns of events that produce the one or more behaviors, to obtain a time-series training data, and with development of a knowledge-driven simulator, sensor data sets are generated for typical resident behavior, in accordance with definable activity patterns and pattern influencers of interest;

transforming, the time-series training data, to obtain a feature engineered training data, wherein the feature engineered training data is associated with the one or more behaviors;

training, a machine learning (ML) model with the feature engineered training data, to obtain a trained ML model for the one or more behaviors;

applying, the trained ML model on a real-world data, to predict an outcome data relevant to the one or more behaviors;

determining, one or more deviations in the initial behavior knowledge model, by comparing the time-series training data, the real-world data, and the outcome data; and fine-tuning, the initial behavior knowledge model with the determined one or more deviations, to derive a behavior knowledge model.

10. The one or more non-transitory machine-readable information storage mediums of claim 9, wherein fine-tuning the initial behavior knowledge model with the one or more deviations, is performed until the time-series training data arising out of the behavior knowledge model is dose to the real-world data.

11. The one or more non-transitory machine-readable information storage mediums of claim 9, wherein building the initial behavior knowledge model associated with the one or more behaviors of the subject to be monitored, using (i) the domain knowledge, and (ii) the historical real-world data, comprises:

identifying the one or more behaviors of interest associated with the subject to be monitored;

determining a range of variations associated with each of the one or more behaviors, using (i) the domain knowledge, and (ii) the historical real-world data;

identifying one or more visible signs associated with each of the one or more behaviors, using the domain knowledge;

incorporating one or more structures and one or ore processes that produce the one or more behaviors and the associated one or more visible signs, using the domain knowledge;

adding (i) one or more process parameters associated with each process of the one or more processes, (ii) one or more occurrence patterns of events that trigger the one or more processes, and (iii) one or more relationships between characteristics of the one or more structures and the one or more behaviors; and determining values and coefficients associated with (i) the one or more process parameters, (ii) the one or more occurrence patterns, and (iii) one or more relationships, by reverse engineering the historical real-world data, wherein the reverse engineering creates a series of signature specifications to process sensor data, recognize events and processes of interest, along with process parameters and associated characteristics such as durations, and occurrence patterns.

12. The one or more non-transitory machine-readable information storage mediums of claim 11, wherein:

(i) a structure of the one or more structures, is an adjacency data of the environment in which the subject to be monitored; and (ii) a process of the one or more processes is a traversal data determined based on the corresponding structure.

* * * * *